United States Patent [19]

Hauck et al.

[11] 4,101,723
[45] Jul. 18, 1978

[54] SUBSTITUTED PIPERAZINOPROPANOLS

[75] Inventors: Frederic P. Hauck, Somerville; Rita T. Fox, Princeton; John R. Watrous, Pennington, all of N.J.

[73] Assignee: E. R. Squibb & Sons, Inc., Princeton, N.J.

[21] Appl. No.: 784,888

[22] Filed: Apr. 5, 1977

[51] Int. Cl.² .................. C07D 401/04; C07D 295/08
[52] U.S. Cl. ...................................... 544/360; 424/250; 544/394; 560/256
[58] Field of Search .................. 260/268 BC; 560/256

[56] References Cited

U.S. PATENT DOCUMENTS

| 3,894,031 | 7/1975 | Hauck et al. | 260/268 BC |
| 3,947,446 | 3/1976 | Witte et al. | 260/268 BC |

Primary Examiner—Paul M. Coughlan, Jr.
Attorney, Agent, or Firm—Lawrence S. Levinson; Merle J. Smith; Donald J. Barrack

[57] ABSTRACT

Compounds having the formula

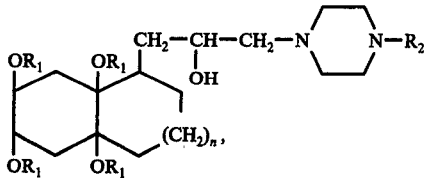

and the pharmaceutically acceptable salts thereof, wherein $R_1$ is alkanoyl; $R_2$ is aryl or pyridinyl; and $n$ is 0, 1 or 2; have useful hypotensive properties.

16 Claims, No Drawings

SUBSTITUTED PIPERAZINOPROPANOLS

BACKGROUND OF THE INVENTION

Cyclitol derivatives having the formula

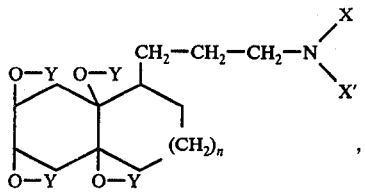

wherein Y is hydrogen or alkanoyl, the group —NXX' is a heterocyclic nitrogen containing group, and n is 0, 1 or 2 are encompassed by the discosure of U.S. Pat. No. 3,894,031, issued July 8, 1975. Among the heterocyclic groups disclosed are piperazino, (lower alkyl)piperazino, di(lower alkyl)piperazino, (lower alkoxy)piperazino, (hydroxy-lower alkyl)piperazino, (alkanoyloxy-lower alkyl)piperazino, (hydroxy-lower alkoxy-lower alkyl)piperazino, and (carbo-lower alkoxy)piperazino. The treatment of hypertension is one of the utilities for the compounds disclosed by the patent.

Aminoalkanol derivatives of a varied nature have been investigated in the field of medicinal chemistry. A review of some of these compounds, and of their various utilities is included in Burger, *Medicinal Chemistry*, second edition, Interscience Publishers, Inc., New York, 1960. Various aminoalkanol derivatives having the general formula

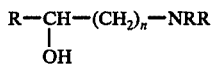

are described as having cholinergic, pressor, central nervous system stimulant, vasoconstrictor and antimalarial activity.

The Burger text, supra., also discusses the hypotensive activity of veratrum alkaloids. The hypotensive activity of crude plant extracts containing veratrum alkaloids is largely attributable to ester alkaloids.

BRIEF DESCRIPTION OF THE INVENTION

Compounds having the formula

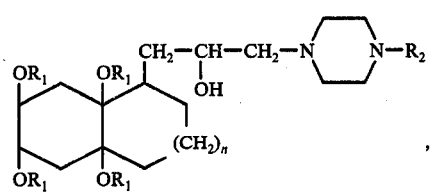

and the pharmaceutically acceptable salts thereof, have cardiovascular activity. In formula I, and throughout the specification, the symbols are as defined below.

$R_1$ is alkanoyl (acetyl is preferred);
$R_2$ is aryl or pyridinyl (1-,2-,3- or 4-pyridinyl); and
$n$ is 0, 1 or 2.

The term "alkanoyl", as used throughout the specification, refers to groups having the formula

wherein Y is alkyl as defined below.

The term "aryl", as used throughout the specification, refers to phenyl or phenyl substituted with one or two halogen (fluorine, chlorine, bromine or iodine), alkyl, trifluoromethyl, alkoxy, or alkylthio groups.

The terms "alkyl", "alkoxy", and "alkylthio", as used throughout the specification, refer to groups having 1 to 6 carbon atoms.

DETAILED DESCRIPTION OF THE INVENTION

The substituted piperazinopropanols of this invention can be prepared by reacting an oxirane compound having the formula

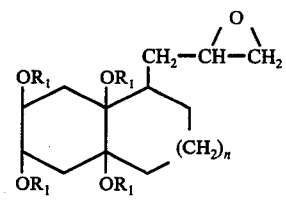

with a piperazine derivative having the formula

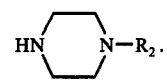

Reaction conditions are not critical, but the reaction proceeds more rapidly when carried out with heating in an organic solvent, or mixture of organic solvents, e.g., a lower alkanol such as ethanol, or an aromatic hydrocarbon such as benzene in combination with a lower alkanol.

The oxirane compounds of formula II are readily obtained from a corresponding compound having the formula

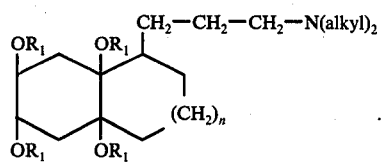

Compounds of formula IV are known; see, for example, U.S. Pat. No. 3,894,031, issued July 8, 1975. Oxidation of a compound of formula IV yields the corresponding N-oxide having the formula

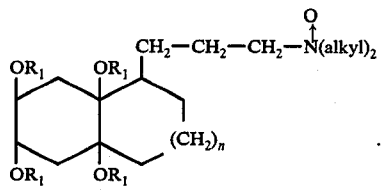

Exemplary of oxidizing agents which may be used are the peracids, e.g., m-chloroperbenzoic acid.

Vacuum pyrolysis of an N-oxide of formula V yields an olefin having the formula

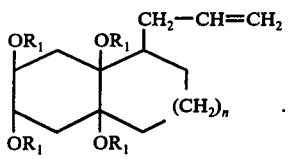

Oxidation of an olefin of formula VI yields the corresponding oxirane compound of formula II. Exemplary of oxidizing agents which may be used are the peracids, e.g., m-chloroperbenzoic acid.

The oxirane compounds of formula II and the olefins of formula VI are novel intermediates which are useful in the preparation of the compounds of formula I, and as such, constitute an integral part of this invention.

The compounds of formula I can be converted to their pharmaceutically acceptable acid-addition salts with both organic and inorganic acids using methods well known in the art. Exemplary salts are hydrohalides (e.g., hydrochloride and hydrobromide), nitrate, phosphate, borate, acetate, tartrate, methanesulfonate, benzenesulfonate, toluenesulfonate and the like.

Formula I includes all stereoisomers and mixtures thereof. Particular stereoisomers are prepared by utilizing as the starting material the compound of formula IV with the corresponding stereoisomerism. The preferred stereoisomers are those in which the $OR_1$ groups are all axial. Particularly preferred are those compounds having the configuration

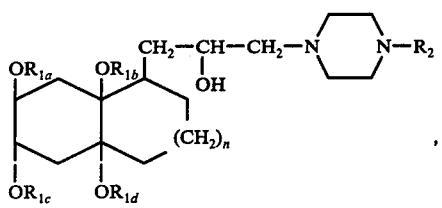

wherein the $OR_{1a}$ and $OR_{1c}$ groups are in the trans configuration as are the $OR_{1b}$ and $OR_{1d}$ groups.

The compounds of formula I show hypotensive properties in hypertensive rats and normotensive dogs. The compounds of this invention, and the pharmaceutically acceptable salts thereof, are useful as hypotensive agents in mammals, e.g., domestic animals such as dogs and cats. Daily doses of from 5 to 50 milligrams per kilogram of animal body weight, preferably about 5 to 25 milligrams per kilogram of animal body weight, can be administered orally or parenterally, in single or divided doses.

The compounds of this invention include indan derivatives having the formula

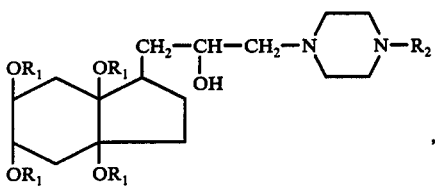

naphthalene derivatives having the formula

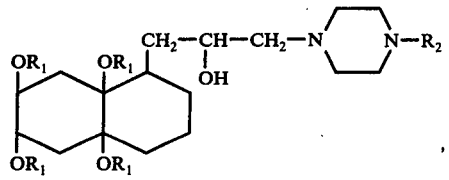

and benzocycloheptane derivatives having the formula

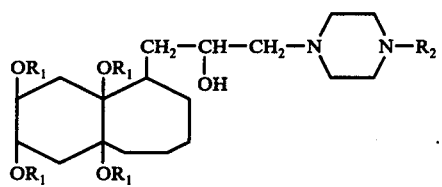

The naphthalene derivatives of formula IX are preferred.

The following examples are specific embodiments of this invention.

EXAMPLE 1

3,4a,5-cis-Decahydro-5-[2-hydroxy-3-[4-(2-methoxyphenyl)-1-piperazinyl]propyl]-2,3;4a,8a-trans-naphthalenetetrol, tetraacetate ester (A)
3,4a,5-cis-Decahydro-5-(3-dimethylaminopropyl)-2,3;4a,8a-trans-naphthalenetetrol, tetraacetate ester, N-oxide A solution of 19.71g of 3,4a,5-cis-5-(3-dimethylamino-propyl)-2,3;4a,8a-trans-naphthalenetetrol, tetraacetate ester and 9.25g of 85% m-chloroperbenzoic acid in 30 ml of chloroform is prepared at 0° C and warmed over 3 hours to room temperature. The solution is then partially evaporated in vacuo and filtered through 520g of neutral Alumina III. Elution with 1 liter each of chloroform and 20% methanolic chloroform gives 24.3g of oil. Crystallization from ethyl acetate gives 14.3g of the N-oxide as a hydroscopic solid, melting point 160°–161° C. The filtrate is evaporated in vacuo to dryness to give an additional 6.38g of solid (IR consistent with crop 1), for a total yield of 20.68g.

(B)
3,4a,5-cis-Decahydro-5-(2-propenyl)-2,3,4a,8a-trans-naphthalenetetrol, tetraacetate ester An amount of 20.2g of the above N-oxide is heated in a vacuum distillation set-up under 30 mm Hg vacuum with nitrogen bleed until all the solid has melted and vigorous gas evolution ceases. The vacuum is improved to 1 mm Hg and the olefin product distilled as a pale yellow liquid, 13.0 g (boiling point 185°–195° at 1 mm Hg), which solidifies on standing. Recrystallization from ether (75 – 100 ml) gives 8.6g of a fine crystalline solid, melting point 151°–155.5° C.

(C)
3,4a,5-cis-Decahydro-5-(oxiranylmethyl)-2,3,4a,8a-trans-naphthalenetetrol, tetraacetate ester A solution of 6.0g of the above tetraacetate-olefin and 3.12g of 85% m-chloroperbenzoic acid in 100 ml of chloroform is prepared at 0° C and stirred at room temperature for about 16 hours. The solution is then suction filtered through a pad of 50g of neutral Alumina III. The alumina is washed with 100 ml of chloroform and the combined filtrates evaporated in vacuo to give 6.4g of a solid, melting point 135°–159° C.

(D)
3,4a,5-cis-Decahydro-5-[2-hydroxy-3-[4-(2-methoxyphenyl)-1-piperazinyl]propyl]-2,3;4a,8a-trans-naphthalenetetrol, tetraacetate ester A solution of 1.5g of 1-(2-methoxyphenyl)piperazine and 3.5g of the above epoxide in 50 ml of absolute ethanol and 20 ml of benzene is stirred in a warm water bath (50°–55° C) for about 20 hours under a drying tube. The solvent is removed in vacuo to give 5.1g of a foam, which is crystallized from ether to give 4.23g of the product as a crystalline solid in two crops. Recrystallization of 3.58g of the solid from ethyl acetate (25–35 ml) gives 2.65g of the title compound, melting point 203–206° C.

Anal. Calc'd. for $C_{32}H_{46}N_2O_{10}$ (618.7 g/m): C, 62.12; H, 7.49; N, 4.53; Found: C, 62.15; H, 7.64; N, 4.43

EXAMPLE 2

3,4a,5-cis-Decahydro-5-[2-hydroxy-3-[4-[3-(trifluoromethyl)-phenyl]-1-piperazinyl]propyl]-2,3;4a,8a-trans-naphthalenetetrol, tetraacetate ester A solution of 2.75g of 3,4,5a-cis-decahydro-5-(oxiranylmethyl)-2,3;4a,8a-trans-naphthalenetetrol, tetraacetate ester and 1.3g of N-($\alpha,\alpha,\alpha$-trifluoro-m-tolyl)-piperazine in 20:50 benzene-absolute ethanol is heated to 55°–60° C for 18 hours. The solution is evaporated in vacuo and the residue is crystallized from ethyl acetate-hexane to give 2.7g of solid in three crops. Recrystallization from ethyl acetatehexane gives 1.85g of material. The 1.85g of material is combined with 0.75g from a previous run and recrystallized to give 2.0g of the title compound, melting point 150°–204° C.

Anal. Calc'd. for $C_{32}H_{43}N_2O_9F_3$ (657.7 g/m): C, 58.52; H, 6.60; N, 4.27; F, 8.68; Found: C, 58.30; H, 6.63; N, 4.13; F, 8.56

EXAMPLE 3

3,4a,5-cis-5-[3-[4-[2-(Ethylthio)phenyl]-1-piperazinyl]-2-hydroxypropyl]-decahydro-2,3;4a,8a-trans-naphthalenetetrol, tetraacetate ester A solution of 2.6g of 3,4,5a-cis-decahydro-5-(oxiranylmethyl)-2,3;4a,8a-trans-naphthalenetetrol, tetraacetate ester and 1.4g of N-[(2-ethylthio)phenyl]piperazine in 20 ml of benzene-50ml of absolute ethanol is stirred at 57° C for about 16 hours. The solution is evaporated in vacuo and the residue crystallized from ether to give 3g of solid. Two recrystallizations from ethyl acetate-methanol give 2.2g of the title compound, melting point 230°–232° C.

Anal. Calc'd. for $C_{33}H_{48}N_2O_9S$ (648.82 g/m): C, 61.09; H, 7.46; N, 4.32; S, 4.94; Found: C, 61.27; H, 7.74; N, 4.33; S, 5.00

EXAMPLE 4

3,4a,5-cis-Decahydro-5-[2-hydroxy-3-[4-(2-pyridinyl)-1-piperazinyl]propyl]-2,3;4a,8a-trans-naphthalenetetrol, tetraacetate ester 3,4,5a-cis-Decahydro-5-(oxiranylmethyl)-2,3;4a,8a-trans-naphthalenetetrol, tetraacetate ester, (2.108g) is dissolved in 50 ml of absolute ethanol and 20 ml benzene. Freshly distilled 1-(2-pyridyl)piperazine (.766g) is added and the resulting solution is heated to 50° C±5°, with stirring for 15 hours. Solvent is removed in vacuo, and the resulting foam is taken up in 250 ml of ethanol from which it immediately crystallizes to yield 2.3g of crystalline solid. The solid is recrystallized from ethyl acetate to yield 1.26g crystalline solid, melting point 225°–229° C.

EXAMPLES 5–13

Following the procedure of Example 1, but substituting the piperazine derivative listed in column I for 1-(2-methoxyphenyl)piperazine, yields the compound listed in column II.

| | Column I | Column II |
|---|---|---|
| 5 | 1-phenylpiperzine | 3,4a,5-cis-decahydro-5-[2-hydroxy-3-(4-phenyl-1-piperazinyl)propyl]-2,3;4a,8a-trans-naphthalenetetrol, tetraacetate ester |
| 6 | 1-(2,6-dibromophenyl)piperazine | 3,4a,5-cis-decahydro-5-[2-hydroxy-3-[4-(2,6-dibromophenyl)-1-piperazinyl]propyl]-2,3;4a,8a-trans-naphthalenetetrol, tetraacetate ester |
| 7 | 1-(2-iodophenyl)piperazine | 3,4a,5-cis-decahydro-5-[2-hydroxy-3-[4-(2-iodophenyl)-1-piperazinyl]propyl]-2,3;-4a,8a-trans-naphthalenetetrol, tetraacetate ester |
| 8 | 3,4a,5-cis-decahydro-5-[2-azine | hydroxy-3-[4-(2-fluorophenyl)-1-piperazinyl]propyl]-2,3;4a,-8a-trans-naphthalenetetrol, tetraacetate ester |
| 9 | 1-(3,4-dimethylphenyl)piperazine | 3,4a,5-cis-decahydro-5-[2-hydroxy-3-[4-(3,4-dimethylphenyl)-1-piperazinyl]propyl]-2,3;4a,8a-trans-naphthalenetetrol, tetraacetate ester |
| 10 | 1-(2,6-dimethoxyphenyl)piperazine | 3,4a,5-cis-decahydro-5-[2-hydroxy-3-[4-(2,6-dimethoxyphenyl)-1-piperazinyl]propyl]-2,3;4a,8a-trans-naphthalenetetrol, tetraacetate ester |
| 11 | 1-(1-pyridyl)piperazine | 3,4a,5-cis-decahydro-5-[2-hydroxy-3-[4-(1-pyridinyl)-1-piperazinyl]propyl]-2,3;-4a,8a-trans-naphthalenetetrol, tetraacetate ester |
| 12 | 1-(3-pyridyl)piperazine | 3,4a,5-cis-decahydro-5-[2-hydroxy-3-[4-(3-pyridinyl)-1-piperazinyl]propyl]-2,3;-4a,8a-trans-naphthalenetetrol, tetraacetate ester |
| 13 | 1-(4-pyridyl)piperazine | 3,4a,5-cis-decahydro-5-[2-hydroxy-3-[4-(4-pyridinyl)-1-piperazinyl]propyl]-2,3;-4a,8a-trans-naphthalenetetrol, tetraacetate ester |

EXAMPLE 14

3a,5-cis-3a,7a;5,6-trans-Hexahydro-1-[2-hydroxy-3-[4-(2-methoxyphenyl)-1-piperazinyl]propyl]-1H-indene-3a,5,6,7a-tetrol, tetraacetate ester, hydrochloride (1:1)

3a,5-cis-3a,7a;5,6-trans-Hexahydro-1-(3-dimethylaminopropyl)-1H-indene-3a,5,6,7a-tetrol, tetraacetate ester, N-oxide An amount of 2.4g of 85% m-chloroperbenzoic acid is added to a solution of 5.0g of 3a,5-cis-3a,7a;5,6-transhexahydro-1-(3-dimethylaminopropyl) in 50 ml of chloroform at 0°–5° C. The cold bath is removed and the mixture is stirred for 3½ hours under nitrogen. The solution is partially evaporated in vacuo and then chromatographed on 98 g of neutral Alumina III. Elution with chloroform and methanolic chloroform yields, upon evaporation in vacuo, 4.6 g of the N-oxide as a white solid.

3a,5-cis-3a,7a;5,6-trans-Hexahydro-1-(2-propenyl)-1H-indene-3a,5,6,7a-tetrol, tetraacetate ester The above N-oxide (4.6 g) is vacuum pyrolyzed at 160°–190° C under 12 mm Hg vacuum. The product is vacuum distilled to give 2.1 g of crude olefin at 185°–195° C under 0.25 mm Hg vacuum. Further purification by chromatography on 35 g of neutral Alumina III eluted with 15–20% ethyl acetate-hexane yields 1.0 g of the olefin as a white solid.

3a,5-cis-3a,7a;5,6-trans-Hexahydro-1-(oxiranylmethyl)-1H-indene-3a,5,6,7a-tetrol, tetraacetate ester An amount of 0.52 g of 85% m-chloroperbenzoic acid is added to a solution of 1.0 g of olefin in 25 ml of chloroform and the solution stirred for about 16 hours at room temperature. The solution is partially evaporated in vacuo and then filtered through a column of 22 g of neutral Alumina III. Elution with 260 ml of 20–30% ethyl acetate-hexane yields 0.9 g of epoxide as a white solid.

3a,5-cis-3a,7a;5,6-trans-Hexahydro-1-[2-hydroxy-3-[4-(2-methoxyphenyl)-1-piperazinyl]propyl]-1H-indene-3a,5,6,7a-tetrol, tetraacetate ester, hydrochloride (1:1)

A solution of 0.9 g of epoxide and 0.43 g of o-methoxyphenylpiperazine in 20:50 benzene-absolute ethanol is stirred for 18 hours in a 57° C bath. The solvent is removed in vacuo and the residue chromatographed on 25 g of neutral Alumina III. Elution with 150 ml of 25–30% ethyl acetate-hexane yields 0.53 g of forerun (mainly recovered epoxide). Elution with 200 ml of 35–40% ethyl acetate-hexane yields 0.57 g of the product as a free base. The free base is converted to the hydrochloride salt and recrystallized from ethyl acetate-ether to yield 0.5 g of the title compound, melting point 215°–220° C.

Anal. Calc'd. for $C_{31}H_{44}N_2O_{10} \cdot HCl$ (641.16 g/m) C, 58.07; H, 7.08; N, 4.37; Cl, 5.53; Found: C, 57.89; H, 7.00; N, 4.31; Cl, 5.67

EXAMPLE 15

3,4a-cis-Hexahydro-5-[2-hydroxy-3-[4-(2-methoxyphenyl)-1-piperazinyl]propyl]-2,3;4a,9a-trans-benzocycloheptanetetrol, tetraacetate ester

(A)
3,4a-cis-Hexahydro-5-(3-dimethylaminopropyl)-2,3;4a,9a-trans-benzocycloheptanetetrol, tetraacetate ester, N-oxide A solution of 3,4a-cis-hexahydro-5-(3-dimethylaminopropyl)-2,3;4a,9a-trans-benzocycloheptanetetrol, tetraacetate ester (12.8 mmole) and m-chloroperbenzoic acid (2.5 g) in chloroform (100 ml) is prepared at 0° C and gradually warmed to room temperature to yield the title N-oxide.

(B)
3,4a-cis-Hexahydro-5-(2-propenyl)-2,3;4a,9a-trans-benzocycloheptanetetrol, tetraacetate ester The above N-oxide (10.8 mmole) is heated in a vacuum distillation set-up under 30 mm Hg vacuum with nitrogen bleed to yield the title olefin.

(C)
3,4a,5-cis-Hexahydro-5-(oxiranylmethyl)-2,3;4a,9a-transbenzocycloheptanetetrol, tetraacetate ester A solution of the above tetraacetate-olefin (5.9 mmole) and 85% m-chloroperbenzoic acid (1.3 g) in chloroform (50 ml) is prepared in 0° C and stirred at room temperature for about 16 hours to yield the title epoxide.

(D)
3,4a-cis-Hexahydro-5-[2-hydroxy-3-[4-(2-methoxyphenyl)-1-piperazinyl]propyl]-3,3;4a,9a-trans-benzocycloheptanetetrol, tetraacetate ester A solution of 1-(2-methoxyphenyl)piperazine (5.0 mmole) and the above epoxide (5.0 mmole) in absolute ethanol (50 ml) and benzene (20 ml) is stirred in a warm water bath (50°–55° C) for about 20 hours under a drying tube to yield the title compound.

What is claimed is:

1. A compound having the formula

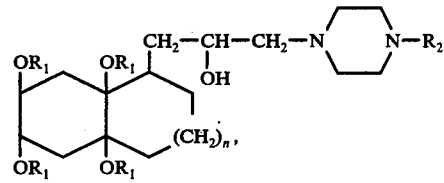

or a pharmaceutically acceptable salt thereof, wherein
$R_1$ is alkanoyl;
$R_2$ is pyridinyl, phenyl, or phenyl substituted with 1 or 2 halogen, alkyl, trifluoromethyl, alkoxy or alkylthio groups; and
$n$ is 0, 1 or 2;
and wherein the terms alkyl, alkoxy and alkylthio refer to groups having 1 to 6 carbon atoms and the term alkanoyl refers to groups having 1 to 7 carbon atoms.

2. A compound in accordance with claim 1 wherein $n$ is 0.

3. A compound in accordance with claim 1 wherein $n$ is 1.

4. A compound in accordance with claim 1 wherein $n$ is 2.

5. A compound in accordance with claim 3 wherein $R_1$ is acetyl.

6. A compound in accordance with claim 5 wherein $R_2$ is pyridinyl.

7. A compound in accordance with claim 6 wherein $R_2$ is 2-pyridinyl.

8. A compound in accordance with claim 5 wherein $R_2$ is phenyl.

9. A compound in accordance with claim 5 wherein $R_2$ is phenyl substituted with 1 or 2 halogen, alkyl, trifluoromethyl, alkoxy or alkylthio groups.

10. The compound in accordance with claim 1, 3,4a,5-cis-decahydro-5-[2-hydroxy-3-8 4-(2-methoxyphenyl)-1-piperazinyl]propyl]-2,3;4a,8-trans-naphthalenetetrol, tetraacetate ester.

11. The compound in accordance with claim 1, 3,4a,5-cis-decahydro-5-[2-hydroxy-3-[4-[3-(trifluoromethyl)phenyl]-1-piperazinyl]propyl]-2,3;4a,8a-trans-naphthalenetetrol, tetraacetate ester.

12. The compound in accordance with claim 1, 3,4a,5-cis-5-[3-[4-[2-(ethylthio)phenyl]-1-piperazinyl]-2- hydroxypropyl]-decahydro-2,3;4a,8a-trans-naphthalenetetrol, tetraacetate ester.

13. The compound in accordance with claim 1, 3,4a,5-cis-decahydro-5-[2-hydroxy-3-[4-(2-pyridinyl)-1-piperazinyl]-propyl]-2,3;4a,8a-trans-naphthalenetetrol, tetraacetate ester.

14. The compound in accordance with claim 1, 3a,5-cis-3a,7a;5,6-trans-hexahydro-1-[2-hydroxy-3-[4-(2-methoxyphenyl)-1-piperazinyl]propyl]-1H-indene-3a,5,6,7a-tetrol, tetraacetate ester, monohydrochloride.

15. A compound having the formula

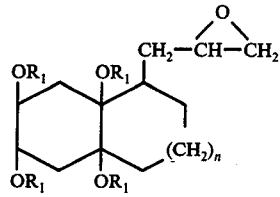

wherein $R_1$ is alkanoyl having 1 to 7 carbon atoms and $n$ is 0, 1 or 2.

16. A compound having the formula

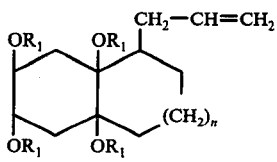

wherein $R_1$ is alkanoyl having 1 to 7 carbon atoms and $n$ is 0, 1 or 2.

* * * * *

UNITED STATES PATENT AND TRADEMARK OFFICE
CERTIFICATE OF CORRECTION

PATENT NO. : 4,101,723
DATED : July 18, 1978
INVENTOR(S) : Frederic P. Hauck et al It is certified that error appears in the above-identified patent and that said Letters Patent are hereby corrected as shown below:

Column 4, line 51, "2,3,4a" should read --2,3;4a--.

Column 4, line 64, "2,3,4a" should read --2,3;4a--.

Column 6, Example 5, Column I, "phenylpiperzine" should read --phenylpiperazine--.

Column 6, Example 5, Column II, Line 4, "napththalenetetrol" should read --naphthalenetetrol--.

Column 6, Example 7, Column I, "4a,8a-trans-naphthalene-" should be inserted in Column II, Line 4.

Column 6, Example 8, Column I, "3,4a,5-cis-decahydro-5-[2-" should be inserted in Column II, Line 1.

Column 6, Example 8, Column I, "3,4a,5-cis-decahydro-5-[2-" should be deleted and --1-(2-fluorophenyl)piper- -- should be inserted.

Column 8, Line 60, "3-8" should read --3-[--.

Signed and Sealed this

Sixth Day of February 1979

[SEAL]

Attest:

RUTH C. MASON
*Attesting Officer*

DONALD W. BANNER
*Commissioner of Patents and Trademarks*